(12) United States Patent
Machek

(10) Patent No.: US 6,187,025 B1
(45) Date of Patent: Feb. 13, 2001

(54) VASCULAR FILTER

(75) Inventor: James E. Machek, Roanoke, VA (US)

(73) Assignee: Noble-Met, Ltd., Salem, VA (US)

( * ) Notice: Under 35 U.S.C. 154(b), the term of this patent shall be extended for 0 days.

(21) Appl. No.: 09/392,907

(22) Filed: Sep. 9, 1999

(51) Int. Cl.$^7$ ................................................. A61M 29/00
(52) U.S. Cl. ............................................. 606/200; 604/96
(58) Field of Search ................................. 606/200, 194; 604/96

(56) References Cited

U.S. PATENT DOCUMENTS

| | | | |
|---|---|---|---|
| 4,779,628 | 10/1988 | Machek | 128/772 |
| 5,695,519 | 12/1997 | Summers et al. | 606/200 |
| 5,769,816 * | 6/1998 | Barbut et al. | 604/96 |
| 5,779,716 | 7/1998 | Cano et al. | 606/114 |
| 5,928,261 * | 7/1999 | Ruiz | 606/200 |

* cited by examiner

*Primary Examiner*—Gary Jackson
(74) *Attorney, Agent, or Firm*—Timothy M. Honeycutt

(57) ABSTRACT

Various vascular filters are provided. In one aspect, a vascular filter is provided that includes a tubular sleeve and a core positioned in the sleeve that is axially deployable therefrom. A shape-memory wire is spiraled around the core and has a first portion unfurled from the core to define a hoop. The hoop is expandable from a retracted shape to a expanded shape when the core is deployed from the sleeve. A filter is provided that has a first end coupled to the core and a rim coupled to the hoop. The integration of the hoop with the shape-memory wire provides for excellent tip flexibility with enhanced resistance to structural failure.

22 Claims, 4 Drawing Sheets

VASCULAR FILTER

BACKGROUND OF THE INVENTION

1. Field of the Invention

This invention relates generally to vascular devices, and more particularly to a vascular filter that employs an expandable filter to capture particles in the blood stream.

2. Description of the Related Art

A large variety of vascular disorders are currently diagnosed and treated using non-invasive intervention techniques. Examples of such abnormalities are legion, including such conditions as atherosclerosis, arteriosclerosis, cerebral and coronary thrombosis, and aortic aneurysm, to name just a few. The types of vascular intervention techniques used to treat such conditions include, for example, coronary artery by-passes and grafts, aortic aneurism repair, and carotid angioplasty, coronary angioplasty, and intercranial angioplasty with or without the stent placement. Although these procedures are employed in several different parts of the patient's body and involve different medical indications, they share several common attributes. To begin with, each of these procedures, in one form or another, involves the movement of one or more catheter or catheter-like devices through the artery or vein affected by the occlusion, aneurism, or other disorder. Proper catheter positioning requires navigation through often constricted and highly irregular vessels, and is impacted by the stiffness of the catheter tip. Stiffer catheters are more difficult to maneuver. In addition, each of these vascular intervention techniques either creates or is subject to the risk of the movement of emboli downstream from the distal end of the implanted catheter or catheters. Such migrating emboli may be the result of the intentional fragmentation of material within the vessel, such as plaque or a thrombus, or may be the result of dislodged emboli that developed naturally elsewhere in the patient's body.

Migrating emboli can lead to a variety of problematic medical conditions. Depending on the size and origin of the emboli, the patient can develop cardiac valve and vessel occlusion and damage, renal artery occlusion or phlebitis. If the emboli circulate to and lodge in the vascular tree of the head and neck, the result may be ischemic stroke.

Various mechanisms have been developed to capture embolic material dislodged during vascular intervention. One such conventional design consists of a flexible tubular sheath which temporarily encloses one or more wire frames. The wire frames are constructed of a shape memory effect alloy in the super elastic state and are deplorable from the sheath to form two loops about which a filter sack is attached. The wire frames are attached to an elongated wire linkage by a relatively rigid crimp junction. Two disadvantages associated with this conventional design are the propensity of the wire frames to dislodge from the crimp junction and the inherent stiffness of the crimp junction. As noted above, it is desirable for the distal end of any vascular intervention catheter or catheter-like device to be highly flexible at its distal end to facilitate navigation through irregular and narrow vascular passageways. The crimp junction presents a relatively rigid impediment to bending motion of this conventional design.

Another conventional vascular filter device consists of a straight shaped memory wire that is partially positioned within a flexible tube. The wire is folded back upon itself and the two ends thereof are connected proximally to a handle assembly. The middle portion of the wire is crimped. A portion of the wire distal to the crimp is projectable out of the sleeve in the form of a loop to which a filter bag is attached. The loop is expandable and retractable by application of axial force to the two proximal ends of the wire. To deploy the loop, axial compression is applied to the two proximal ends of the wire to force the loop to project from the sleeve. Retraction involves application of axial tension to the proximal ends of the wire to collapse the loop. A disadvantage associated with this conventional design is the fact that the extremely fine portions of the wire must be capable of transmitting compressive force without binding in order for the loop to successfully deploy. With such fine gauge wires undergoing compression, there is the potential for buckling and binding within the lumen of the sleeve.

Another conventional design employs a wire loop that is coupled to the coiled wire of a guiding catheter. The guiding catheter includes a tubular core about which the guide wire is coiled. The wire loop is positioned eccentrically with respect to the tubular core and is connected to the coiled wire by welding. One difficulty associated with this conventional design is the dedicated eccentric positioning of the loop presents a limit on the minimum diameter vessel that may be navigated and requires more vessel flow area that might otherwise be occupied by another instrument. Another disadvantage is the requirement of a welded junction between the wire loop and the coiled guide wire. The integrity of the junction between the coiled wire and the wire loop is critical for the proper operation of this conventional filter as well as the safety of the patient. As the diameters of the parts joined by welding are quite small, the precision and quality of the weld are critical to the successful joining of these two components.

The present invention is directed to overcoming or reducing the effects of one or more of the foregoing disadvantages.

SUMMARY OF THE INVENTION

In accordance with one aspect of the present invention, a vascular filter is provided that includes a tubular sleeve and a core positioned in the sleeve that is axially deplorable therefrom. A shape-memory wire is spiraled around the core and has a first portion unfurled from the core to define a hoop. The hoop is expandable from a retracted shape to an expanded shape when the core is deployed from the sleeve and compressible from the expanded shape to the retracted shape when the core is returned the sleeve. A filter is provided that has a first end coupled to the core and a rim coupled to the hoop.

In accordance with another aspect of the present invention, a vascular filter is provided that includes a core and a tubular sleeve positioned around the core that is axially moveable thereon from a first position to a second position. A shape-memory wire is spiraled around the core and has a first portion unfurled from the core to define a hoop. The hoop is expandable from a retracted shape to an expanded shape when the sleeve is moved from the first position to the second position compressible from the expanded shape to the retracted shape when the sleeve is moved from the second position back to the first position. A filter is provided that has a first end coupled to core and a rim coupled to the hoop.

In accordance with another aspect of the present invention, a vascular filter is provided that includes a tubular sleeve and a core positioned in the sleeve that is moveable axially relative the sleeve. A tubular member is coupled to the sleeve and has a plurality of openings. A shape-memory wire is provided that has a first end and a second end coupled to the core and an intermediate portion defining a hoop. The first and second ends are projectable from the openings. A filter is provided that has a first end coupled to the sleeve and a rim coupled to the hoop. The hoop is expandable when the core is advanced axially and the first and second ends of the shape-memory wire are projected from the openings and contracted when the core is withdrawn axially.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
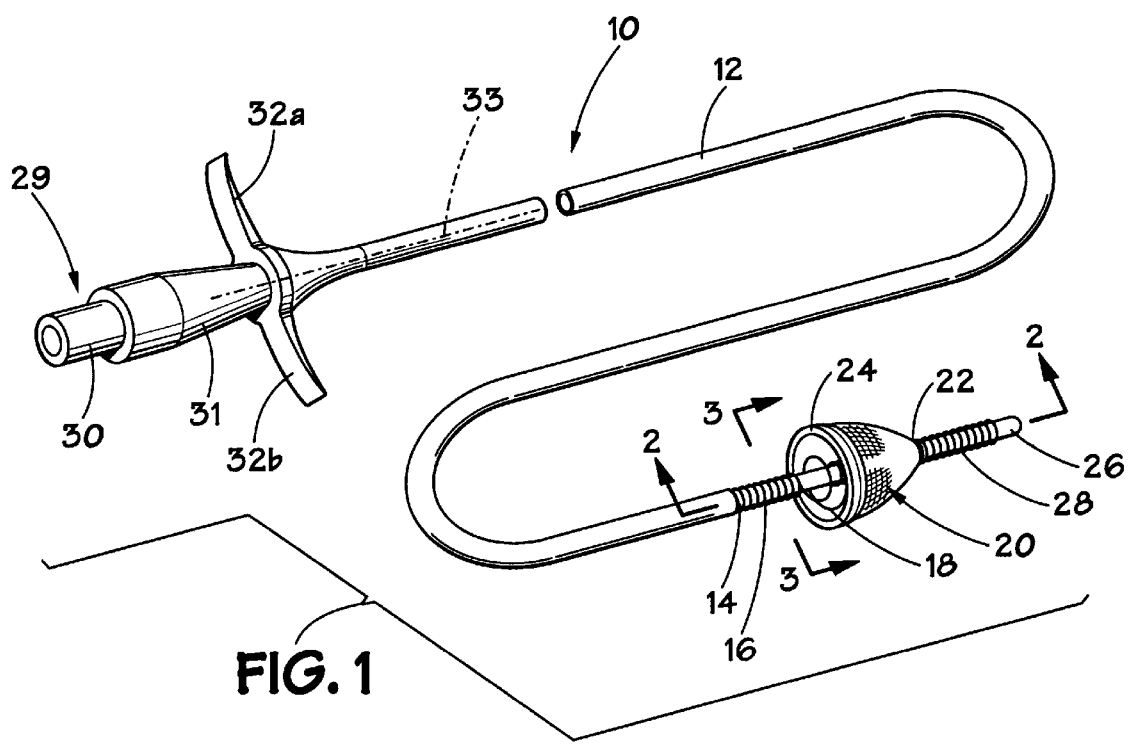
FIG. 1 is a pictorial view of an exemplary embodiment of a vascular filter in accordance with the present invention.

In the drawings described below, reference numerals are generally repeated where identical elements appear in more than one figure. Turning now to the drawings, and in particular to FIG. 1, there is shown a pictorial view of an exemplary embodiment of a vascular filter 10 which is designed to be inserted into a patient's body vessel to capture migrating emboli. The vascular filter 10 includes an elongated tubular sleeve 12 in which a core 14 is positioned. The sleeve 12 and the core 14 are of such length that they are shown broken. A shape memory wire 16 is spiraled around the core 14. A portion of the shape memory wire 16 is unfurled to define a hoop 18. A filter 20 is provided for capturing migrating emboli. The filter 20 has a proximal rim 24 that is coupled to the hoop 18 and a distal end 22 connected to the core 14. The distal end 26 of the core 14 is provided with a coiled wire 28, the structure and function of which will be described more fully below.

The shape memory wire 16, the sleeve 12 and the core 14 may be coupled proximally to a handle assembly 29 that is designed to enable the physician to spatially manipulate the vascular filter 10 and to initiate relative axial sliding movement between the sleeve 12 and the core 14. The handle assembly 29 includes a tubular handle 30 that is coupled to the proximal end of the core 14 by crimping, welding or other fastening methods. The distal end of the handle 30 is threadedly engaged to a tubular insert 31 that is, in turn, threadedly engaged to the proximal end of the sleeve 12. The proximal end of the sleeve 12 is provided with radially projecting wings 32a and 32b. In an exemplary embodiment, the filter 10 is introduced into a patient's vessel and spatially manipulated via the handle assembly 29 to the targeted site in the vessel. The hoop 18 and the filter 20 are initially positioned inside the sleeve 12. To deploy the filter 20, the sleeve 12 is withdrawn proximally to release the hoop 18. It is desirable to maintain hand contact with the core 14 while the sleeve 12 is moved axially. In this regard, the insert 31 is disconnected from the sleeve 12 and the proximal end of the sleeve 12 is split longitudinally by pulling radially on the wings 32a and 32b and peeling sleeve 12 distally like a banana peel. As the sleeve 12 is peeled back, it may be withdrawn proximally without releasing the handle 30. To facilitate the splitting of the sleeve 12, the exterior of the sleeve 12 is scored longitudinally as indicated by the dashed line 33.

In the illustrated embodiment, the sleeve 12 is moved axially relative to the core 14. However, the skilled artisan will appreciate that the relative axial movement between the sleeve 12 and the core 14 may be accomplished by moving the core 14 axially while holding the sleeve 12 stationary, by moving the sleeve 12 axially while holding the core 14 stationary or by some combination of axial movements of the sleeve 12 and the core 14. In this way, the filter 20 and the hoop 18 may be retracted and compressed inside the sleeve 12 during insertion into a vessel and moved out of the sleeve 12 to the deployed position depicted in FIG. 1 so that the hoop 18 is allowed to expand diametrically to the shape shown to open and fully deploy the filter 20 when the desired site in the vessel is reached.

Figure 2:
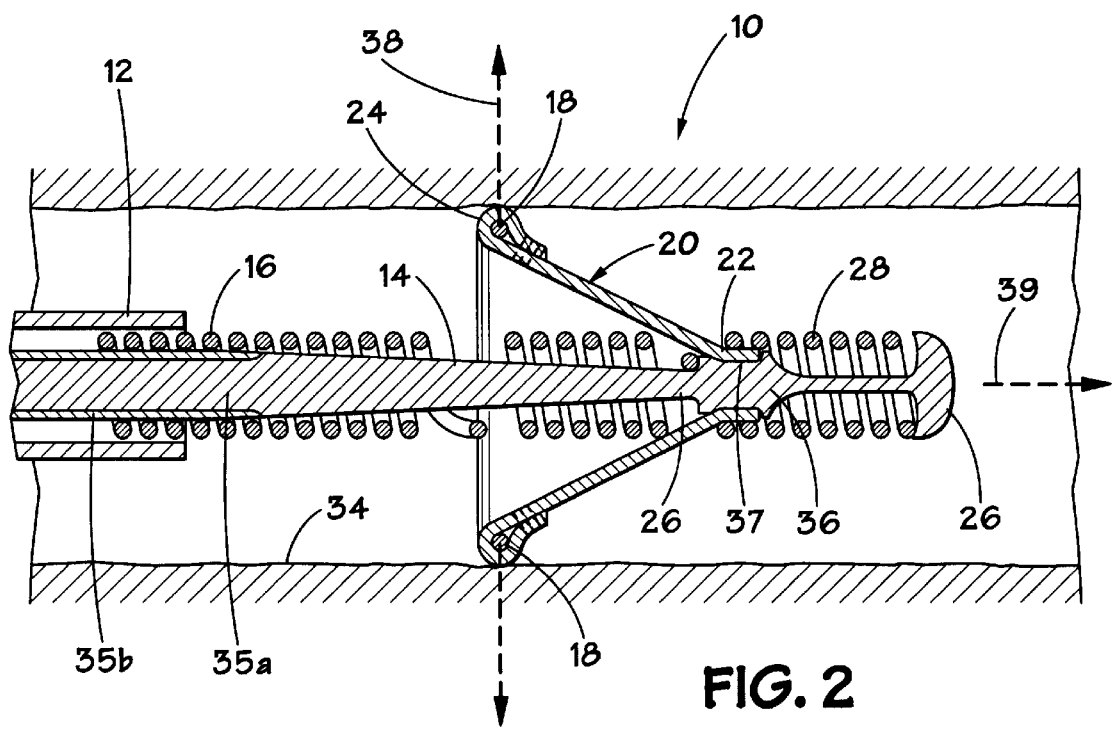
FIG. 2 is a sectional view of FIG. 1 taken at section 2—2 in accordance with the present invention.
Figure 3:
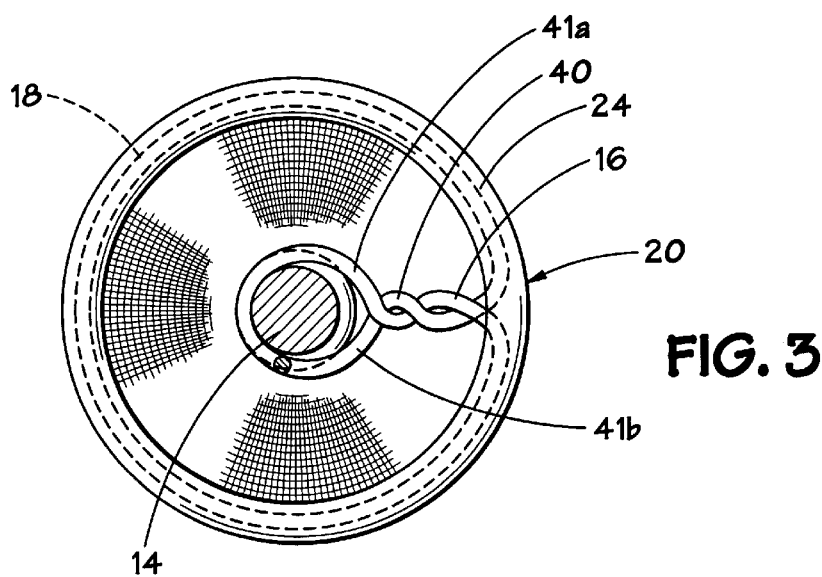
FIG. 3 is a sectional view of FIG. 1 taken at section 3—3 in accordance with the present invention.

The detailed structure of the shape memory wire 16, the core 14 and the filter 20 may be understood by referring now to FIGS. 2 and 3, which are, respectively, sectional views of FIG. 1 taken at sections 2—2 and 3—3. FIG. 2 shows the vascular filter 10 positioned inside a body vessel 34 with the hoop 18 and the filter 20 deployed. The sleeve 12 is designed to provide a smooth-surfaced tubular structure that facilitates ready movement within body vessels. In this regard, the sleeve 12 is advantageously composed of a flexible, biocompatible material, such as silicone, polyurethane, or like materials.

The core 14 is a tubular member that is relatively flexible along its entire length, and particularly near the distal end 26 so that difficult bends and passages along the implantation route can be successfully navigated. The core 14 is advantageously composed of biocompatible materials such as, for example, 316 or 304 stainless steel, MP35N alloy, or the like. A certain degree of flexibility is desirable. However, it is also desirable for the core 14 to exhibit enough rigidity proximally so that compressive forces applied by the physician to the handle 30 are readily transmitted without undue buckling. In this regard, the core 14 may consist of an interior portion 35a of a superelastic material, such as nickel-titanium alloy, and a coating 35b of a higher stiffness material such as 316 or 304 stainless steel. The coating 35b and the interior portion 35a may be extruded or otherwise fabricated together and the portion of the coating 35b proximate the hoop 18 and the filter 20 may be removed thereafter by grinding or the like to ensure high flexibility proximate the filter 20.

The flexibility of the core 14 proximate the filter 20 is further enhanced by tapering the distal end 26 of the core 14 down to a small diameter as shown. The distal end 26 tapers distally for a selected length and then expands in diameter temporarily to define a hub 36 with an external channel 37. Distal to the hub 36, the end tapers to a fine gauge and terminates in portion of the wire 28 melted to form a rounded head which eliminates the possibility of tissue damage.

The rim 24 of the filter 20 is secured to the hoop 18 by folding up and around the hoop 18 and forming an enclosure or hem by securing the overlapped portions to the filter 20 with stitching or application of a biocompatible adhesive. The filter 20 itself, is advantageously a mesh bag composed of a biocompatible mesh material, such as, for example, Dacron, Gore-Tex®, or the like. A mesh configuration is desirable to trap plaque, emboli or other undesirable particles but allow blood to readily pass through. The distal end 22 of the filter 20 is secured to the core 14 by compressing the distal end 22 into the channel 37 of the hub 36 and threading the proximal end of the wire 28 up over the distal end 22 and into the channel 37. The joint may be additionally secured by application of a biocompatible adhesive.

The coiled wire 28 serves as a flex member and as a radiographic marker to enable the distal end 26 of the core 14 to be imaged by fluoroscopy during movement within the patient's body. If desired, an additional radiographic marker may be coupled to the distal end 26. In order to provide the desired radiopaque characteristics for the coiled wire 28, a variety of materials may be used, such as, for example, platinum-iridium alloy wire composed of approximately 90 atomic percent platinum and 10 atomic percent iridium, gold plated tungsten wire, platinum tantalum alloy wire or the like. The coiled wire 28 may be secured to the core 14 by laser spot welding, application of a biocompatible adhesive, or other well known fastening methods. Optionally, the coiled wire 28 may be significantly elongated and nested within the coils of the shape memory wire 16.

Figure 4:
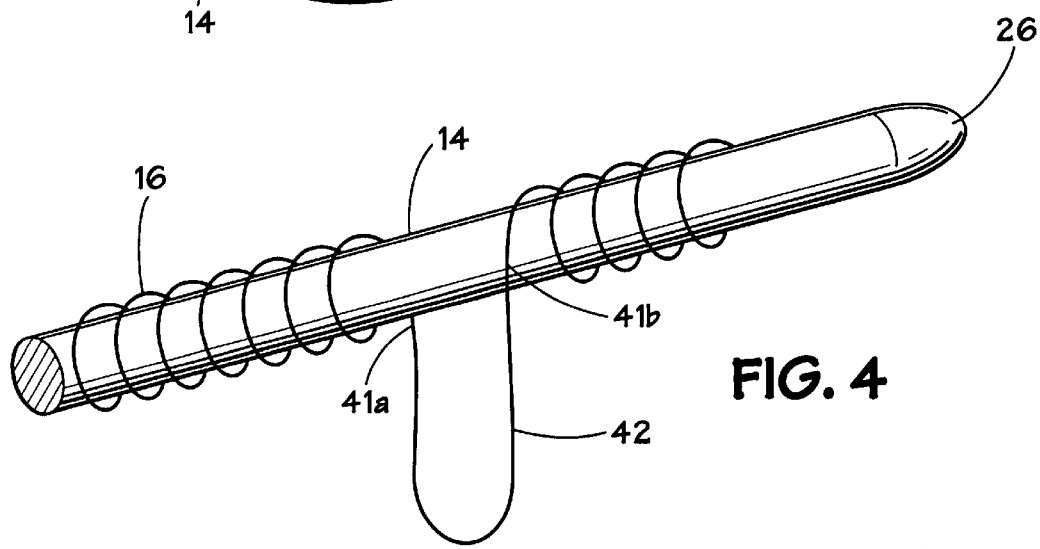
FIG. 4 is a pictorial view of the distal end of the core of the vascular filter depicting the unfurling of a portion of the shape memory wire thereof in accordance with the present invention.
Figure 5:
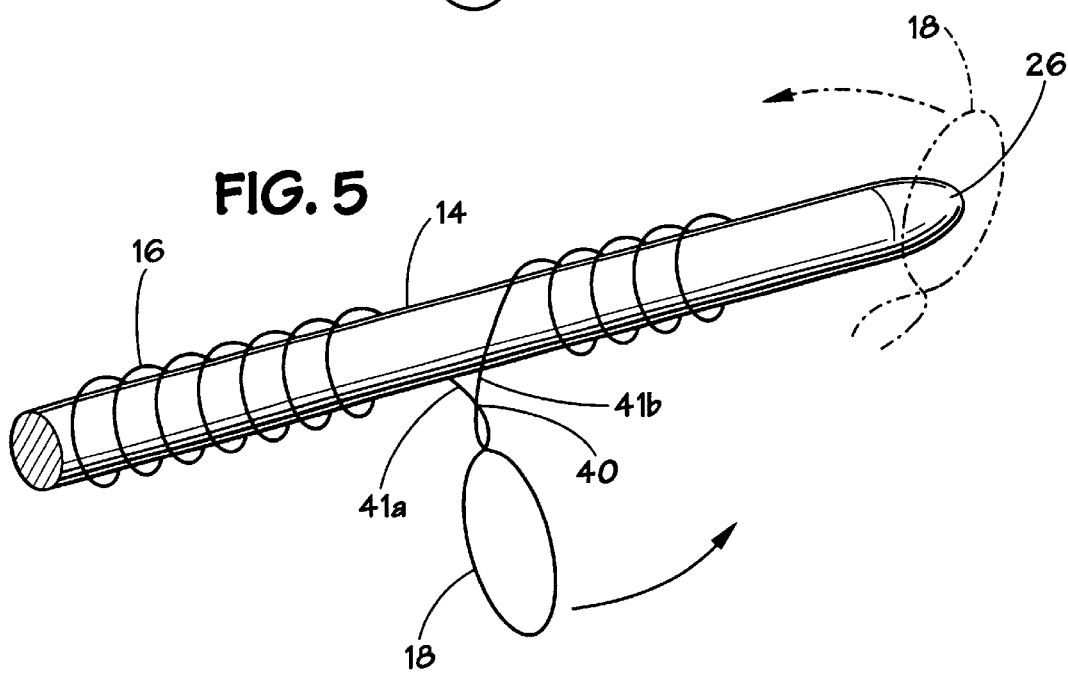
FIG. 5 is a pictorial view like FIG. 4 depicting the deformation and definition of the hoop of the vascular filter of FIG. 1 in accordance with the present invention.

The hoop 18 is defined by unfurling and deforming a portion of the shape memory wire 16. The skilled artisan will appreciate that it is desirable for the plane of the hoop 18, represented by the dashed line 38, to be substantially orthogonal to the longitudinal axis 39 of the core 14. In this way, the flow area of the blood vessel 34 occluded by the filter 20 is maximized. To provide the desired orientation for the hoop 18, a portion of the shape memory wire 16 is unfurled, twisted at 40 near the ends 41a and 41b of the wire 16 that are proximate the core 14, and the defined hoop 18 is then folded back over the distal end 26 of the core 14 and deformed back into the position depicted in FIGS. 2 and 3. This operation may be understood by referring now also to FIGS. 4 and 5, which are simplified pictorial views of the distal end 26 of the core 14 and the shape memory wire 16 with the filter 20 not shown for simplicity of illustration. As shown in FIG. 4, a portion 42 of the shape memory wire 16 is unfurled. At this juncture, the portion 42 retains the generally helical configuration of the remaining portions of the shape memory wire 16. Next, and as shown in FIG. 5, the ends 41a and 41b of the portion 42, which are proximate the core 14, are twisted at 40 to define the hoop 18. At this point, the hoop 18 is eccentrically positioned with respect to the core 14, and as described below, could be used to support the filter 20. However, to achieve concentric positioning of the hoop 18 relative to the core 14 as shown in FIGS. 2 and 3, the hoop 18 is next folded back and looped over the distal end 26 of the core 14 and then deformed proximally to provide the configuration depicted in FIGS. 2 and 3. The superelastic character of the shape memory wire 16 enables the substantial bending and twisting of the shape memory wire 16 necessary to define the hoop 18 to be carried out without substantial kinking or other undesired deformation.

Figure 6:
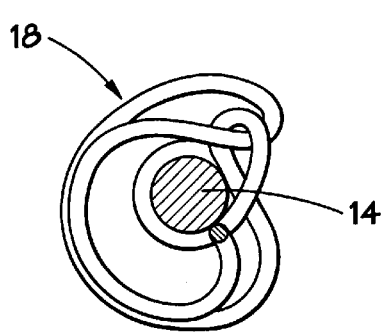
FIG. 6 is an end view of an alternate exemplary embodiment of a shape memory wire and hoop in accordance with the present invention.
Figure 7:
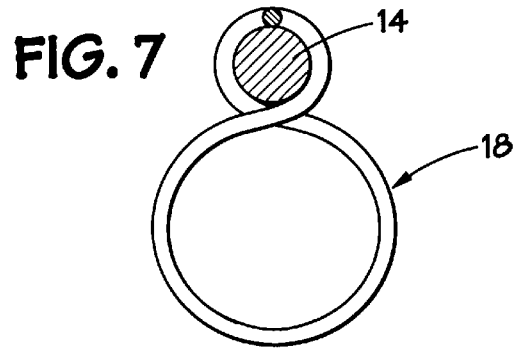
FIG. 7 is an end view like FIG. 6 depicting another alternate exemplary embodiment of the shape memory wire and hoop in accordance with the present invention.
Figure 8:
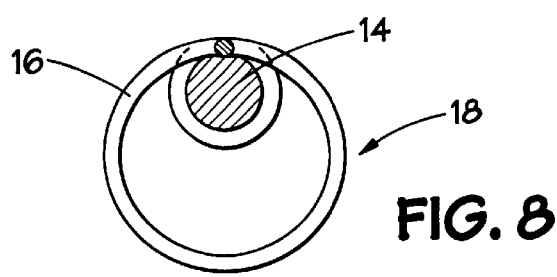
FIG. 8 is a end view like FIG. 7 depicting another alternate exemplary embodiment of the shape memory wire and hoop in accordance with the present invention.

The hoop 18 may be provided with a myriad of different arrangements. For example, FIG. 6 depicts a sectional view like FIG. 3 but with the filter 20 removed for simplicity of illustration. As shown in FIG. 6, the hoop 18 is provided with a concentric position relative to the core 14, similar to the arrangement shown in FIG. 3. However, in this illustrative embodiment, the crossover or twisting of the ends of the shape memory wire is accomplished at a greater distance from the outer diameter of the core 14 as shown. FIGS. 7 and 8 show two sectional views similar to FIG. 6 of other alternate illustrative embodiments wherein the hoop 18 is eccentrically positioned with respect to the core 14. As shown in FIG. 7, the hoop 18 is eccentrically disposed and defined by twisting proximate the outer diameter of the core 14 in much the same way as the hoop 18 is depicted in FIG. 5 prior to being wrapped around the distal end 26 of the core. As shown in FIG. 8, the hoop 18 is defined by unfurling a portion of the shape memory wire 16 and compacting the coils longitudinally but without twisting to achieve the desired eccentric position of the hoop 18.

In any of the aforementioned embodiments, the shape memory wire 16 is subjected to severe bending both during the initial deformation to define the hoop 18 and during subsequent deployment and retraction. Accordingly, the shape-memory wire 16 is advantageously composed of a material or alloy that exhibits not only biocompatibility but also excellent flexibility. In an exemplary embodiment, the shape memory wire 16 is composed of a shape memory alloy exhibiting superelasticity such as, for example, nickel titanium alloy with between about 50 and 52 atomic percent nickel. Superelasticity is desirable to avoid kinking or other undesirable plastic deformation of the hoop 18 and other sections of the unfurled portion of the wire 16 both before and after deployment of the core 14 from the sleeve 12. The wire 16 may be single filar as depicted or multi-filar as desired, and may be secured to the core 14 by welding, application of a biocompatible adhesive, or other joining methods. In an exemplary embodiment, the wire 16 is laser welded at various points along the length of the core 14. To facilitate the relative sliding movement of the core 14 and the wire 16 relative to the sleeve 12, the shape memory wire 16 may be coated with a lubricious material, such as Teflon, and/or a lubricious material such as parylene may be introduced between the inner diameter of the sleeve 12 and the outer diameter of the core 14.

The deployment and retraction of the vascular filter 10 may be understood by referring now to FIGS. 1 and 2. Initially, and prior to insertion into the patient's body, the core 14 is retracted axially to a retracted position relative to the sleeve 12 in which the hoop 18 is positioned inside and compressed by the inner diameter of the sleeve 12. The retracted position may be such that the entirety of the filter 20 may be positioned inside the sleeve 12 although a relatively isodiametric profile may be obtained if less than the entirety of the filter 20 is positioned inside the sleeve 12. Following insertion to the desired point in the patient's body, the sleeve 12 is moved axially away from the distal end 26 or the core is moved axially out of the sleeve 12 or some combination of the two movements is performed to move the hoop 18 out of the sleeve 12. As the hoop 18 is moved out of the sleeve 12, it expands to the deployed position depicted in FIG. 2 and opens the filter 20. If it is desired to retract the filter 20 and hoop 18, the core 14 may be moved relative to the sleeve 12 so that the distal end of the sleeve 12 contacts the radially projecting portion of the shape memory wire 16, in this case, the twisted portion 40, causing the twisted portion 40 to bend toward the core 14. As the twisted portion 40 bends towards the core 14, the hoop 18 collapses radially and may be withdrawn into the sleeve 12.

Figure 9:
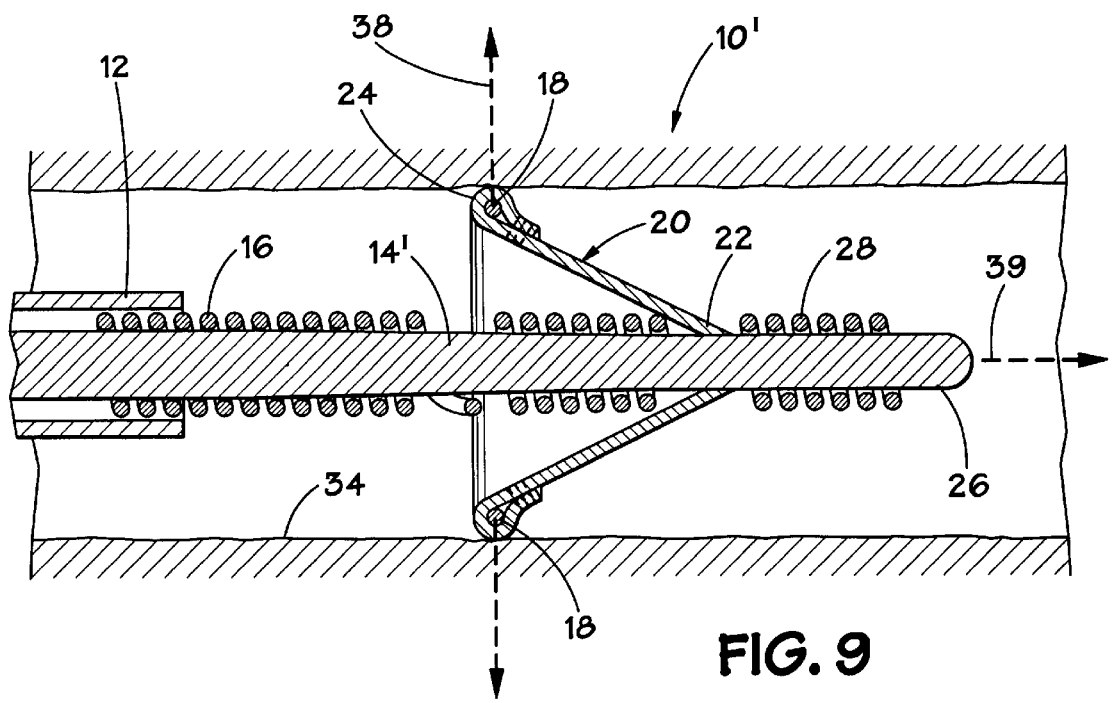
FIG. 9 is a sectional view of an alternate exemplary embodiment of the vascular filter taken from a section like FIG. 2 in accordance with the present invention

An alternate exemplary embodiment of a vascular filter 10' may be understood by referring now to FIG. 9, which is a sectional view like FIG. 2. In this embodiment, the core, now designated 14', is tapered for flexibility. However, the hub 26 depicted in FIG. 2 is eliminated and the distal end 22 of the filter 22 is secured to the core 14 by application of a biocompatible adhesive. In other aspects, the filter 10' may be substantially identical to the filter 10 described above. Note also that the distal end 22 may be secured to the core 14 via connection to either the shape memory wire 16 or the coiled wire 28 as an option.

Figure 10:
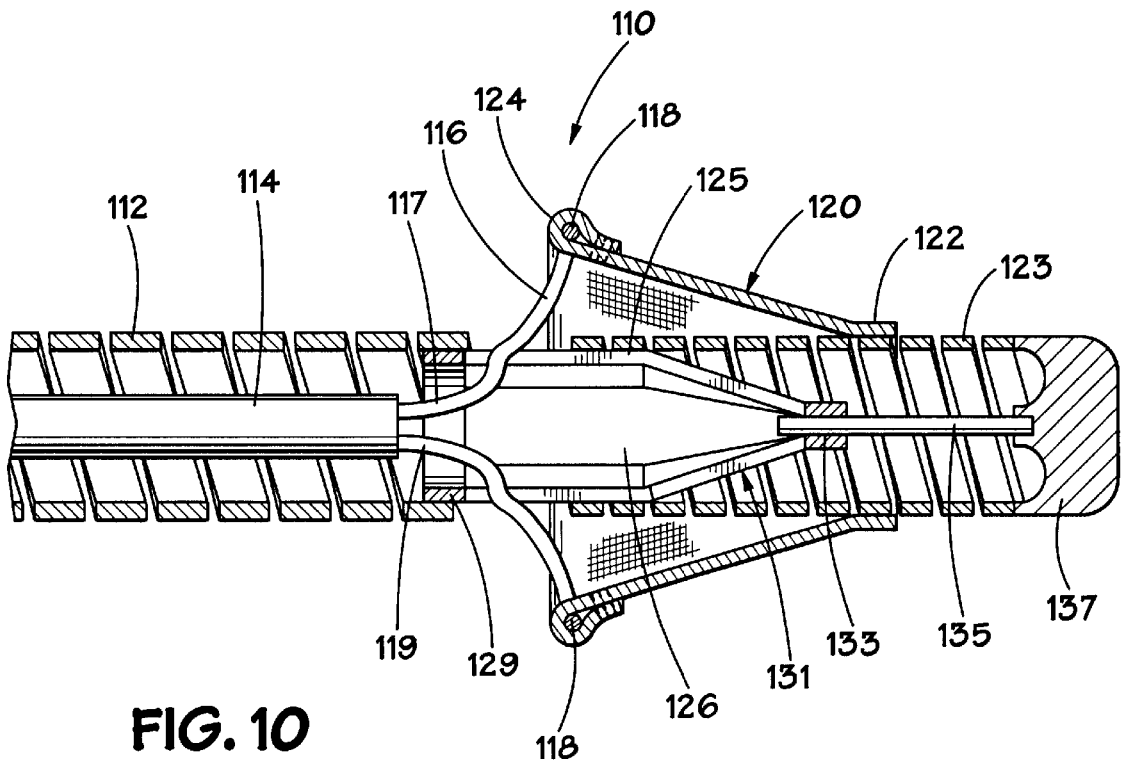
FIG. 10 is a sectional view of another alternate exemplary embodiment of the vascular filter taken from a section like FIG. 2 in accordance with the present invention.
Figure 11:
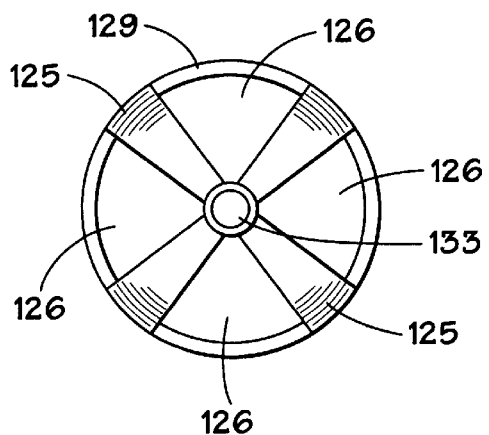
FIG. 11 is an end view of a tubular member of a vascular filter depicted in FIG. 9 in accordance with the present invention.

Another alternate exemplary embodiment of a vascular filter 110 may be understood by referring now to FIGS. 10 and 11. FIG. 10 is a sectional view like FIG. 2. This illustrative embodiment includes a tubular sleeve 112 and a tubular core 114 axially movable therein. The core 114 includes a shape memory wire 116 that has a first end 117 coupled to the core 114, an intermediate portion that defines a hoop 118, and a second end coupled to the core 114. A filter 120 is provided that has a distal end 122 secured to the outer diameter of a flexible sleeve 123 and a rim 124 that is secured to the hoop 118 by overlapping and forming an enclosure or hem as described above.

A tubular member 125 is provided and includes a plurality of openings 126 through which the first and second ends 117 and 119 of the shape memory wire 116 project. The structure of the tubular member 125 may be further understood by referring also to FIG. 11, which is a right end view of the tubular member 125 shown separated from the vascular filter 110. The tubular member 125 includes an annular rim 129 which is secured to the inner diameter of the sleeve 112 by crimping, welding, or application of a biocompatible adhesive. The distal end 131 of the tubular member 125 has a generally conical configuration and terminates in a bore 133 in which the proximal end of a flexible wire 135 is positioned and secured. The distal end of the wire 135 is coupled to an end piece 137 that is, in turn, secured to the distal end of the flexible sleeve 123. The proximal end of the flexible sleeve 123 is secured to the tubular member 125 by welding, crimping, or application of a biocompatible adhesive.

The sleeve 112 is designed to provide a flexible elongated and spatially manipulatable tubular structure which the physician can readily manipulate through the desired vascular pathway during insertion. In the illustrated embodiment, the sleeve 112 consists of a coiled flat wire composed of a biocompatible metallic material such as, for example, 304 stainless steel, 316 stainless steel, MP35N or the like. Note that the spacing between the coils of the wire is shown exaggerated for clarity of illustration. Optionally, although not shown in the drawings, the sleeve 112 may consist of a wire reinforced silicone or polyurethane tubing of the type frequently used in guiding catheters.

The core 114 is designed to provide a flexible elongated member that may be moved axially relative to the sleeve 112 to project and, alternatively retract the ends 117 and 119 of the shape memory wire 116 from the tubular member 125 to expand or retract the hoop 118 and thus filter 120. The core 114 may be a unitary tubular structure, a hollow tubular structure, a braided cable or the like. In an exemplary embodiment, the core consists of a nickel titanium alloy braided cable and the shape memory wire 116 consists of a filar of the cable unfurled and deformed into the circular shape of the hoop 118. The nickel-titanium alloy may have the composition disclosed above.

The tubular member 125 is designed to provide a flexible structural member for connection to the sleeve 112 and for providing a framework through which the ends 117 and 119 of the shape memory wire 116 may be projected and retracted to manipulate the diameter of the hoop 118. The tubular member 125 is advantageously composed of a biocompatible metallic material, such as, for example, 304 stainless steel, 316 stainless steel, MP35N alloy, nickel titanium alloy, or combinations of these or the like.

The flexible sleeve 123 may be configured substantially like the sleeve 112. In the illustrated embodiment, the flexible sleeve 123 is similarly configured as a coiled flat wire, with an outer diameter that is slightly smaller than the outer diameter of the sleeve 112. The sleeve 123 may have the same or a larger diameter than the sleeve 112 as desired.

The flexible wire 135 is designed to provide a stable but relatively compliant bending of the distal end of the filter 110. The wire 135 may be fabricated from the same types of materials used to fabricate the sleeve 112 and may be secured in the bore 133 by crimping, welding or application of a biocompatible adhesive.

The end piece or cap 137 is provided with a rounded distal end to lessen the potential for tissue damage. The end cap 137 may be composed of the same types of materials used to fabricate the sleeve 112 and, if desired, may be composed of a radiopaque material that facilitates fluoroscopy imaging, such as, platinum iridium alloy or the like.

The operation of the vascular filter 110 may be understood by referring now to FIGS. 10 and 11. Prior to insertion into the patient's body, the core 114 is retracted axially away from the end cap 137, causing the ends 117 and 119 of the shape memory wire to retract through the openings 126 and collapsing the hoop 118 against the sleeve 123 or against the tubular member 125. In this configuration, the filter 120 is effectively collapsed against the sleeve 123 or the tubular member 125, providing a relatively isodiametric profile that facilitates insertion through the various vascular pathways to the desired site in the patient's body. When the desired site within the patient's body is reached, the core 114 is advanced axially toward the end cap 137. As the core 114 is advanced, the ends 117 and 119 of the wire 116 project out through the openings 126, enabling the hoop 118 to expand diametrically and deploy the filter 120. To remove the vascular filter 110, the process is reversed. The core 114 is retracted axially away from the end cap 137, causing the hoop 118 and the filter 120 to collapse against the sleeve 123 or the tubular member 125.

Figure 12:
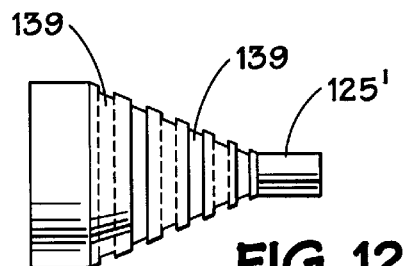
FIGS. 12 and 13 are respective side and end views of an alternate exemplary embodiment of the tubular member of the vascular filter of FIG. 9 in accordance with the present invention.
Figure 13:
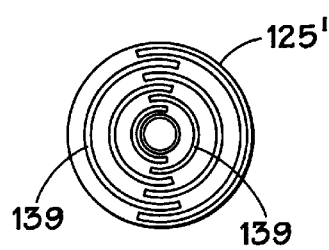

The arrangement of the tubular member 125 depicted in FIGS. 10 and 11 is subject to a myriad of different possibilities. FIGS. 12, 13, 14 and 15 depict respective side and end views of two illustrative alternate embodiments. Referring initially to FIGS. 12 and 13, the tubular member, now designated 125', may be configured with a plurality of radial openings or slots 139. The openings 139 serve the same function as the openings 126 depicted in FIGS. 10 and 11. However, the radial positioning of the openings 139 provides for a greater bending flexibility by the tubular member 125'. This enhanced bending flexibility translates into enhanced maneuverability through tight and irregular passageways.

Figure 14:
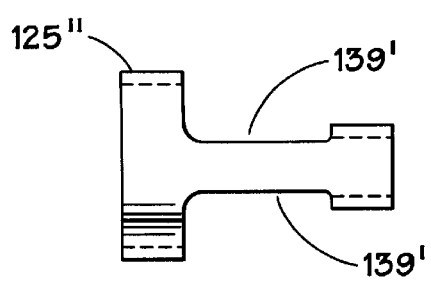
FIGS. 14 and 15 are respective side and end views of another alternate exemplary embodiment of the tubular member of the vascular filter of FIG. 9 in accordance with the present invention.
Figure 15:
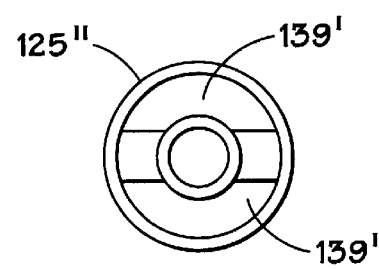

Another alternate exemplary embodiment may be understood by referring now to FIGS. 14 and 15. In this embodiment, the tubular member, now designated 125", is configured similarly to the tubular member 125 depicted in FIGS. 10 and 11. However, FIGS. 14 and 15 illustrate that the number of openings, now designated 139', is subject to wide variation, and in this case, consists of two openings 139'.

The various embodiments disclosed herein provide a mechanism for emboli filtration that exhibits excellent bending flexibility and mechanical reliability. The hoop 18 or 118 is integral with the wire 16 or 166, eliminating potentially troublesome welds or stiff crimp members. Axial force is transmitted through the supporting core 14, 14' or 114, eliminating the need to place fine gauge wires in potentially buckling and binding compression.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A vascular filter, comprising:

a tubular sleeve;

a core positioned in the sleeve and being axially deployable therefrom;

a shape-memory wire spiraled around the core and having a first portion unfurled from the core to define a hoop, the hoop being expandable from a retracted shape to an expanded shape when the core is deployed from the sleeve and compressible from the expanded shape to the retracted shape when the core is returned the sleeve; and a filter having a first end coupled to the core and a rim coupled to the hoop.

2. The vascular filter of claim 1, wherein the hoop is substantially concentric with the core when in the expanded shape.

3. The vascular filter of claim 1, wherein the hoop is substantially eccentric with the core when in the expanded shape.

4. The vascular filter of claim 1, wherein the shape-memory wire is superelastic.

5. The vascular filter of claim 1, comprising a radiographic marker coupled to the core distal to the shape-memory wire.

6. The vascular filter of claim 5, wherein the radiographic marker comprises a wire spiraled around the core distal to the shape-memory wire.

7. The vascular filter of claim 1, wherein the core has an external channel, the first end of the filter being retained in the channel by a wire threaded into the external channel over the first end of the filter.

8. A vascular filter, comprising:

a core;

a tubular sleeve positioned around the core and being axially moveable thereon from a first position to a second position;

a shape-memory wire spiraled around the core and having a first portion unfurled from the core to define a hoop, the hoop being expandable from a retracted shape to an expanded shape when the sleeve is moved from the first position to the second position and compressible from the expanded shape to the retracted shape when the sleeve is moved from the second position back to the first prosition; and a filter having a first end coupled to the core and a rim coupled to the hoop.

9. The vascular filter of claim 8, wherein the hoop is substantially concentric with the core when in the expanded shape.

10. The vascular filter of claim 8, wherein the hoop is substantially eccentric with the core when in the expanded shape.

11. The vascular filter of claim 8, wherein the shape-memory wire is superelastic.

12. The vascular filter of claim 8, comprising a radiographic marker coupled to the core distal to the shape-memory wire.

13. The vascular filter of claim 12, wherein the radiographic marker comprises a wire spiraled around the core distal to the shape-memory wire.

14. The vascular filter of claim 8, wherein the core has an external channel, the first end of the filter being retained in the channel by a wire threaded into the external channel over the first end of the filter.

15. A vascular filter, comprising:

a tubular sleeve;

a core positioned in the sleeve and being moveable axially relative the sleeve;

a tubular member coupled to the sleeve and having a plurality of openings;

a shape-memory wire having a first end and a second end coupled to the core and an intermediate portion defining a hoop, the first and second ends being projectable from the openings; and a filter having a first end coupled to the sleeve and a rim coupled to the hoop, the hoop being expandable when the core is advanced axially and the first and second ends of the shape-memory wire are projected from the openings and contracted when the core is withdrawn axially.

16. The vascular filter of claim 15, wherein the openings comprise slots.

17. The vascular filter of claim 16, wherein the slots are positioned around the circumference of the tubular member at staggered axial distances.

18. The vascular filter of claim 15, comprising an axially disposed flexible wire coupled distally to the tubular member and an end cap coupled to the flexible wire.

19. The vascular filter of claim 15, wherein the sleeve comprises a coiled flat wire.

20. The vascular filter of claim 15, wherein the core comprises a braided shape-memory wire cable having a plurality of filars.

21. The vascular filter of claim 20, wherein the shape-memory wire comprises a portion of one of the plurality of filars.

22. The vascular filter of claim 15, wherein the sleeve comprises a first coiled flat wire coupled to the tubular member and a second coiled flat wire coupled to the tubular member distal to the first coiled flat wire.

\* \* \* \* \*

UNITED STATES PATENT AND TRADEMARK OFFICE
CERTIFICATE OF CORRECTION

| | |
|---|---|
| PATENT NO. : 6,187,025 B1 | Page 1 of 1 |
| DATED : February 13, 2001 | |
| INVENTOR(S) : James E. Machek | |

It is certified that error appears in the above-identified patent and that said Letters Patent is hereby corrected as shown below:

Claim 1,
Insert -- to -- after "returned".

Signed and Sealed this

Sixteenth Day of October, 2001

*Attest:*

*Attesting Officer*

NICHOLAS P. GODICI
*Acting Director of the United States Patent and Trademark Office*